US006950701B2

(12) United States Patent
Begemann et al.

(10) Patent No.: US 6,950,701 B2
(45) Date of Patent: Sep. 27, 2005

(54) DUAL-CHAMBER PACEMAKER SYSTEM FOR SIMULTANEOUS BI-CHAMBER PACING AND SENSING

(75) Inventors: Malcolm J. Begemann, Velp (NL); Geeske Van Oort, Rosmalen (NL)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 10/024,226

(22) Filed: Dec. 21, 2001

(65) Prior Publication Data

US 2003/0120313 A1 Jun. 26, 2003

(51) Int. Cl.$^7$ ................................................ A61N 1/36
(52) U.S. Cl. ............................................ 607/9; 607/28
(58) Field of Search ............................ 607/4, 9, 14, 15, 607/36, 28

(56) References Cited

U.S. PATENT DOCUMENTS

| 4,741,342 A | 5/1988 | Stotts |
| 5,720,768 A | 2/1998 | Verboven-Nelissen |
| 2002/0193834 A1 * | 12/2002 | Levine .......................... 607/9 |

FOREIGN PATENT DOCUMENTS

| EP | 0990451 A2 | 4/2000 | |
| WO | WO 00/04950 * | 2/2000 | .......... A61N/1/368 |
| WO | WO 01/36040 A1 | 5/2001 | |

OTHER PUBLICATIONS

International Search Report, PCT/US02/40680 (Sep. 5, 2003).

* cited by examiner

Primary Examiner—Jeffrey R. Jastrzab
Assistant Examiner—Roderick Bradford
(74) Attorney, Agent, or Firm—Girma Wolde-Michael; Daniel G. Chapilc

(57) ABSTRACT

A method of pacing opposing chambers of a heart with a pacing system is provided. The pacing system comprises a first unipolar medical electrical lead having at least one first electrode configured for positioning in a first opposing chamber of the heart, a second unipolar medical electrical lead having at least one second electrode configured for positioning in a second opposing chamber of the heart, an implantable pulse generator operably connected to the first and second unipolar medical electrical leads. The implantable pulse generator further comprises an hermetically sealed housing capable of serving as a can electrode, and means for switching electrode configurations between the first electrode and the can electrode, between the second electrode and the can electrode, between the first electrode and the second electrode and between the second electrode and the first electrode. A primary electrode configuration is determined. A cathode is selected from the first electrode, the second electrode and the can electrode based on the primary electrode configuration. An anode is selected from the first electrode, the second electrode and the can electrode based on the primary electrode configuration. A first pulse is delivered between the cathode and the anode. Systems, programs and devices using the method are also provided.

19 Claims, 13 Drawing Sheets

DUAL-CHAMBER PACEMAKER SYSTEM FOR SIMULTANEOUS BI-CHAMBER PACING AND SENSING

FIELD OF THE INVENTION

The present invention relates to the field of implantable medical devices, and, more particularly, to dual-chamber cardiac pacing systems that are capable of switching electrode configurations when two unipolar leads are disposed in opposing heart chambers (i.e., left and right atria or left and right ventricles).

BACKGROUND OF THE INVENTION

Tachyarrhythmias are episodes of high-rate cardiac depolarizations. Tachyarrhythmias may occur in one chamber of the heart or may be propagated from one chamber to another. Some tachyarrhythmias are sufficiently high in rate to compromise cardiac output from the chamber(s) affected, leading to loss consciousness or death, in the case of ventricular fibrillation or weakness and dizziness in the case of atrial fibrillation. Atrial fibrillation is often debilitating, due to the loss of atrial cardiac output, and may sometimes lead to ventricular fibrillation.

Generally, fibrillation may be terminated by administering high energy level cardioversion/defibrillation shocks or pulses until the fibrillation is terminated. For example, in the context of implantable anti-arrhythmia devices, these pulses may be applied by means of large surface area electrodes on or in the chamber to be defibrillated. However, the high energy level pulses are often sufficient to cause pain to the patient. Thus, it would be desirable to prevent or decrease the occurrence of atrial fibrillation without the delivery of high energy level pulses.

Some exploration has, therefore, been made in the use of pacing level pulses, which stimulate the cardiac tissue at much lower levels than defibrillation pulses, to terminate atrial fibrillation.

Implantable pulse generators (IPGs) that deliver pacing level pulses are well known in the art. These IPGs may deliver pulses to one or more chambers of the heart. Some of these devices provide pacing stimuli to the heart at a predetermined rate. The stimuli may be applied at a fixed rate, on demand, at a rate synchronized to atrial activity or at a rate synchronized to ventricular activity. This type of pacing function may also be used in other devices such as, for example, implantable cardioverter defibrillators (ICDs) or in external pacemakers. Most IPGs include sense amplifier circuitry for detecting intrinsic cardiac electrical activity. Some IPGs also include sensors or sensing electrodes to determine reliably the heart rate (or pacing rate) in a heart under different conditions. Some IPGs are dual-chamber, having both atrial and ventricular leads. These IPGs have a unipolar lead in the ventricle and a unipolar lead in the atrium.

To deliver pacing pulses of sufficient magnitude to have the desired effect, it may be desirable to stimulate or sense more than one chamber of the heart simultaneously. This may be desirable, for example, because the simultaneous stimulation in opposing chambers results in stimulation pulses of higher amplitude or duration. This may also be desirable because stimulation across opposing chambers of the heart stimulates a desired location of tissue that is more difficult to stimulate across only one chamber of the heart. In standard IPGs, a minimum atrio-ventricular delay makes such simultaneous stimulation difficult or impossible. That is, there is a minimum delay between the time a first chamber, for example the left atria, is stimulated/sensed and the time the second chamber, for example the right atria, is stimulated/sensed.

It would also be desirable to provide stimulation to opposing chambers of the heart using standard programming settings and existing fixed connections in an IPG without the addition of further splitters and adapters.

It would also be desirable to provide switchable configurations of electrodes disposed in opposing atria or ventricles of the heart.

Thus, a need exists in the medical arts for simultaneous stimulation and/or sensing of opposing chambers of a heart.

Several methods have been proposed in the prior art for improving an implantable device's ability to administer pacing pulses simultaneously to more than one chamber of a heart.

For example, U.S. Pat. No. 5,514,161 to Limousin, entitled "Methods and Apparatus for Controlling Atrial Stimulation in a Double Atrial Triple Chamber Cardiac Pacemaker", hereby incorporated by reference in its entirety, discloses a double atrial triple chamber pacemaker, which provides simultaneous stimulation to both atria through the provision of a Y connector.

U.S. Pat. No. 5,757,970 to Pouvreau, entitled "System, Adaptor and Method to Provide Medical Electrical Stimulation" discloses an adaptor that permits a single channel of stimulation to be split and provided to two areas of the heart by adjusting the amplitude of the stimulation pulses.

The article "Permanent Multisite Cardiac Pacing" by Barold, et al. in the journal *PACE* discloses the use of a Y connector to split a standard bipolar output into anode and cathode electrodes.

The article "Hemodynamic Benefits of Permanent Atrial Resynchronization Patients with Advanced Inter Atrial Blocks, paced DDD Mode" by Daubert et al. in the journal *PACE* discloses the use of a bifurcated electrode to pace between the right atrium and the coronary sinus in order to pace both atria simultaneously.

As discussed above, the most pertinent prior art patents are shown in the following table:

TABLE 1

| Prior Art Publications | | |
|---|---|---|
| U.S. Pat. No. | Date | Inventor(s) |
| U.S. Pat. No. 5,514,161 | May 7, 1996 | Limousin |
| U.S. Pat. No. 5,757,970 | Aug. 25, 1998 | Pouvreau |

Barold et al. (November 1997) "System, Adaptor and Method to Provide Medical Electrical Stimulation" PACE, Vol. 20, pages 2725–2729.
Daubert et al. (April 1997) "Hemodynamic Benefits of Permanent Atrial Resynchronization Patients with Advanced Inter Atrial Blocks, paced DDD Mode" PACE, Vol. 14, Part II, page 640, #130.

All the publications listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for simultaneously stimulating and/or sensing opposing chambers of the heart. The system of the present invention overcomes at least some of the problems, disadvantages and limitations of the prior art described above, and provides a more efficient and accurate means of stimulating opposing chambers of a heart.

The present invention has certain objects. That is, various embodiments of the present invention provide solutions to one or more problems existing in the prior art respecting the pacing of cardiac tissue. Those problems include, without limitation: (a) difficulty in simultaneous stimulation of opposing chambers of the heart; (b) need to add splitters, adapters and additional circuitry to an existing IPG in order to accomplish simultaneous stimulation; (c) difficulty in determining appropriate sensing configurations using one or more leads; (d) difficulty in optimizing contractions induced in an opposing chamber of the heart; (e) difficulty in varying cathode and anode functions of electrodes disposed in opposing chambers, (f) difficulty in testing and determining which chamber of the heart provides the lowest pacing threshold; (g) difficulty in configuring electrodes already disposed in opposing chambers of the heart to take advantage of the lowest pacing threshold; (h) need to change circuitry or software/firmware in order to switch electrode configurations.

In comparison to known pacing techniques, various embodiments of the present invention provide one or more of the following advantages: (a) ability to provide simultaneous stimulation to opposing chambers of a heart; (b) ability to provide bi-atrial or bi-ventricular stimulation without an atrio-ventricular delay; (c) ability to reversibly select an anode electrode and a cathode electrode for simultaneous stimulation without removing either electrode from its existing connection; (d) ability to switch and/or select electrode configurations of electrodes already disposed in opposing chambers of the heart; (e) ability to switch and/or select polarity of a given electrode already disposed in a chamber of the heart; (f) ability to optimize hemodynamics of induced contractions in an opposing chamber of the heart; (g) ability to test and determine the chamber having the lowest pacing threshold and configure the electrodes to take advantage of the lowest pacing threshold without using specialized lead adapters; and (h) ability to test and determine the chamber having the lowest pacing threshold and configure the electrodes to take advantage of the lowest pacing threshold without removing the leads from the connector block and re-inserting them in different connector receptacles.

Some embodiments of the present invention include one or more of the following features: (a) an IPG capable of providing bi-atrial or bi-ventricular stimulation without an atrio-ventricular delay; (b) an IPG capable of reversibly switching anode and cathode electrodes for simultaneous stimulation without additional adapters or connectors; (c) an IPG capable of testing opposing chambers to determine which chamber has the lowest pacing threshold and of configuring the electrodes to take advantage of the lowest pacing threshold; (d) an IPG in which the polarity of various electrodes is selectable and/or switchable; (e) an IPG capable of providing staggered stimulation to optimize hemodynamics of induced contractions (f) methods of reversibly selecting an anode electrode and a cathode electrode for simultaneous stimulation without removing either electrode from its existing connection; (g) methods of switching and/or selecting electrode configurations of electrodes already disposed in opposing chambers of the heart; (h) methods of switching and/or selecting polarity of a given electrode disposed in a chamber of the heart; and (i) methods of optimizing hemodynamics of induced contractions in an opposing chamber of the heart.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

It is to be understood that the terms "IPG" and "IMD", as employed in the specification and claims hereof, connote an implantable medical device capable of delivering electrical stimuli to cardiac tissue, and include within their scope pacemakers, PCDs, ICDs, etc.

Figure 1:
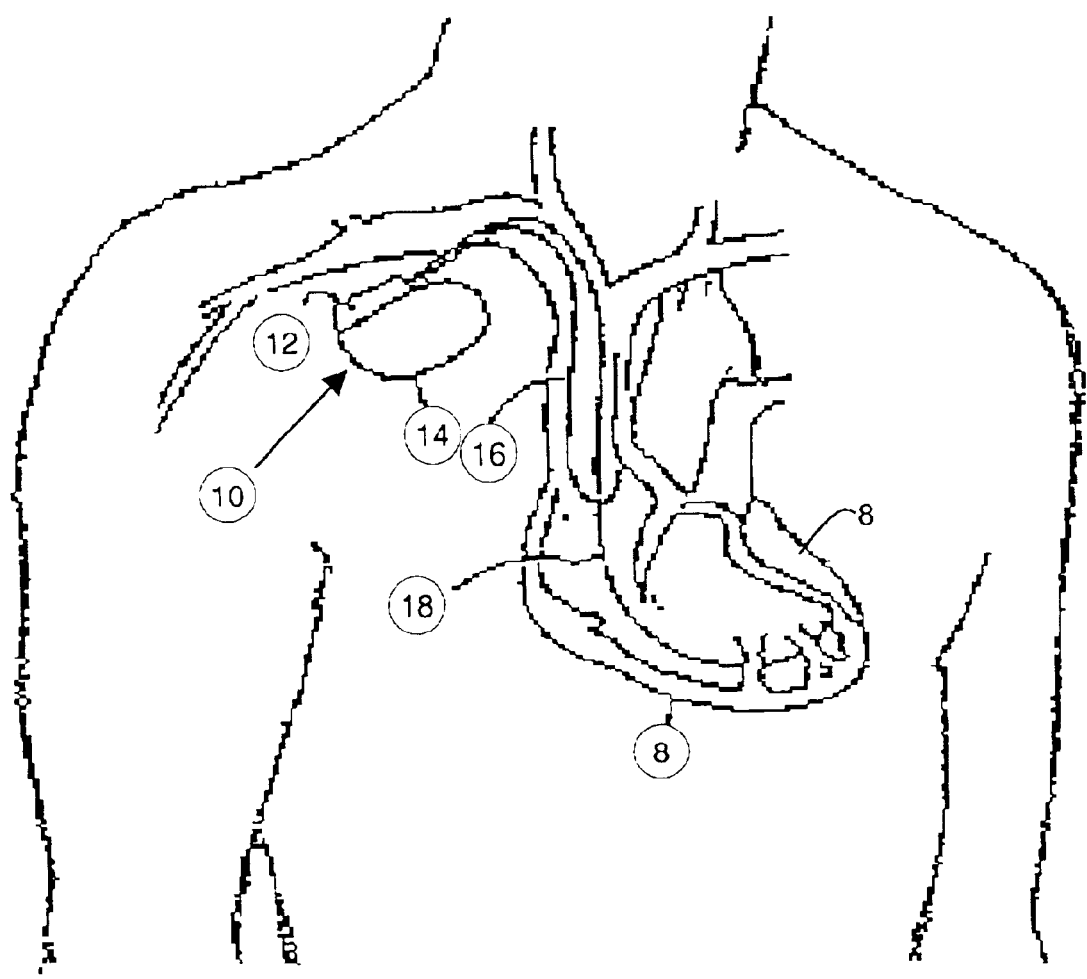
FIG. 1 is a schematic view of one embodiment of an implantable medical device in situ, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Sensing leads 16, 18 may serve, for example, as sensors to sense an atrial response (such as an atrial sensed response or an atrial pulse signal) in accordance with the present invention. One or both of leads 16, 18 may also serve to sense a ventricular response in accordance with the present invention. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
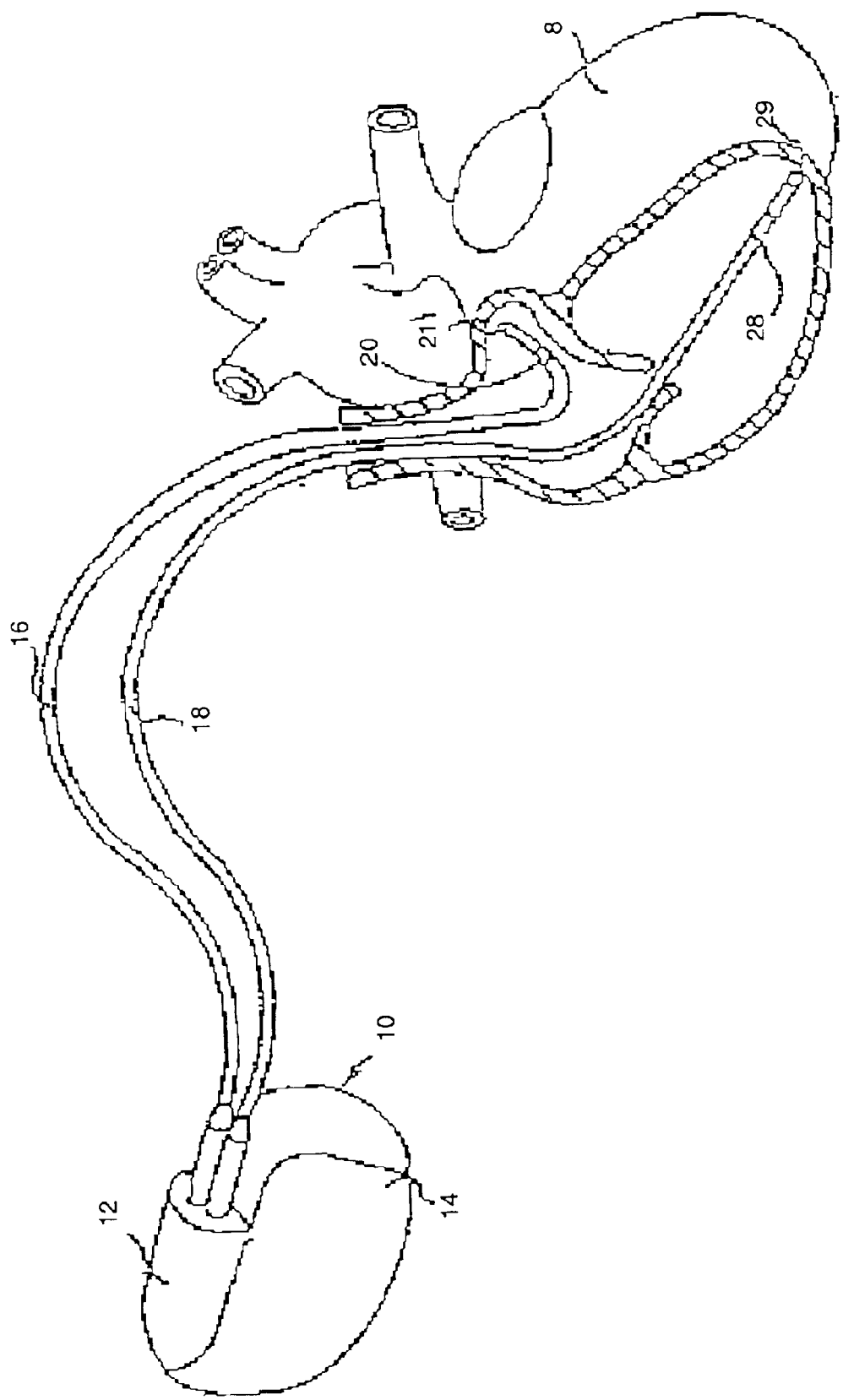
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 may be located in the right atrium. Alternatively, in accordance with the present invention, at least one of atrial electrodes 20, 21 may be located in the left atrium. In one embodiment of the invention, one or both of atrial electrodes 20, 21 may serve as sensors to sense an atrial response (such as an atrial sensed response or an atrial pulse signal) in accordance with the present invention. Ventricular electrodes 28 and 29 at the distal end of ventricular pacing lead 18 are located in the right ventricle. Alternatively, in accordance with the present invention, at least one of the ventricular electrodes 28, 29 may be located in the left ventricle. One or both of ventricular electrodes 28, 29 may also serve to sense a ventricular response in accordance with the present invention.

Figure 3:
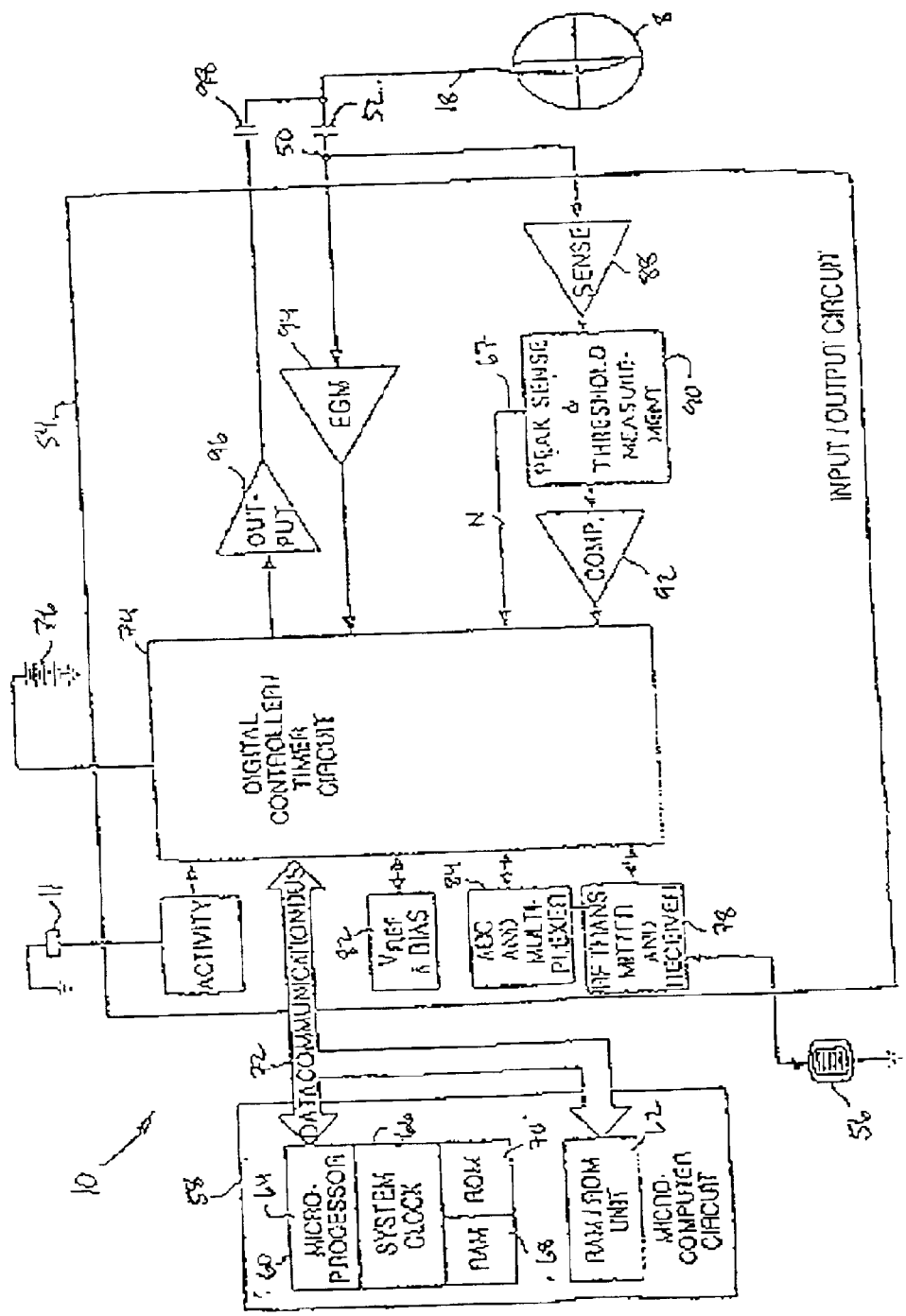
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in U.S. Pat. No. 5,312,453 to Wyborny et al. is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. Accordingly, the rate at which heart 8 is stimulated or beats spontaneously without stimulation may be controlled and/or monitored using software-implemented algorithms or pacing rate functions stored in microcomputer circuit 58.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92.

By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference herein, each in its respective entirety.

Figure 4:
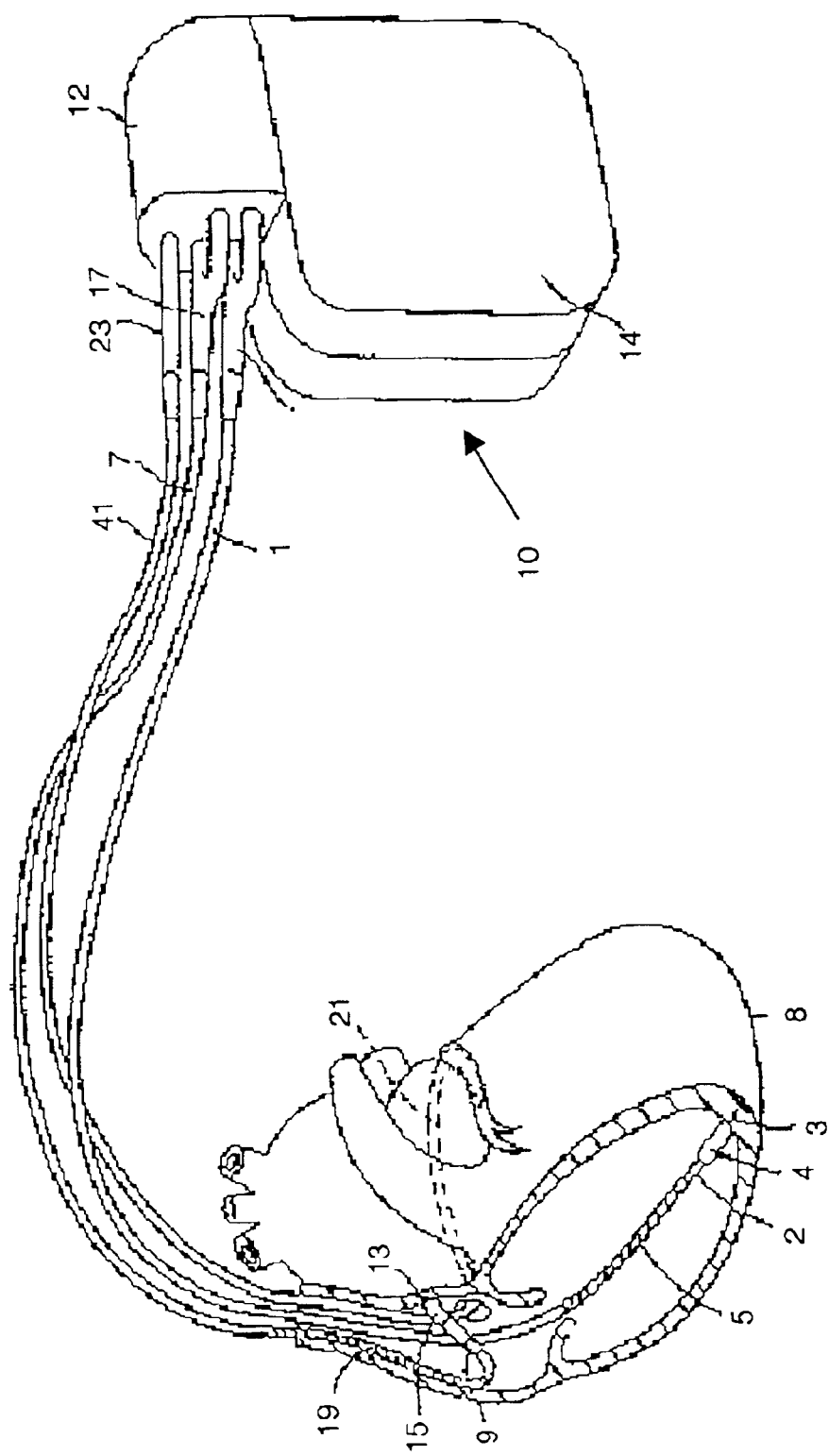
FIG. 4 is a schematic view of another embodiment of an implantable medical device, made in accordance with the present invention.
Figure 5:
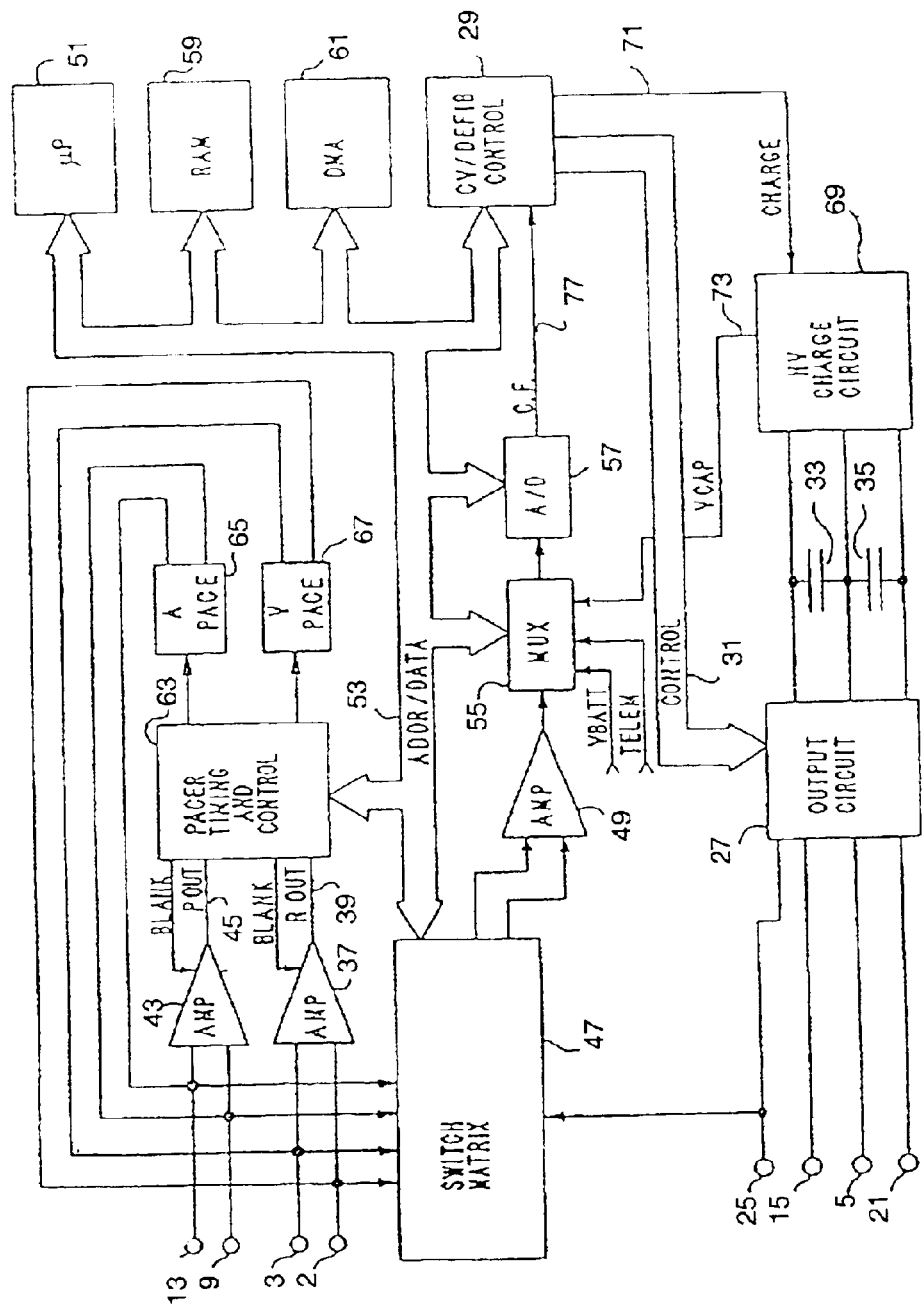
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 may be employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 may be employed for atrial pacing and for sensing atrial depolarizations. Elongated coil electrode 19 is provided proximal to electrode 9 and coupled to the third conductor within lead body 7. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, VVI, DVI, VDD, AAI, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts. Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference herein, each in its respective entirety.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated herein by reference, each in its respective entirety, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference herein, each in its respective entirety, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference herein in its entirety.

An example of circuitry that may be used to control delivery of monophasic pulses is disclosed in U.S. Pat. No. 5,163,427 to Keimel, also hereby incorporated by reference herein in its entirety. Output control circuitry similar to that disclosed in U.S. Pat. No. 4,953,551 to Mehra et al. or U.S. Pat. No. 4,800,883 to Winstrom, both incorporated by reference, each in its respective entirety, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
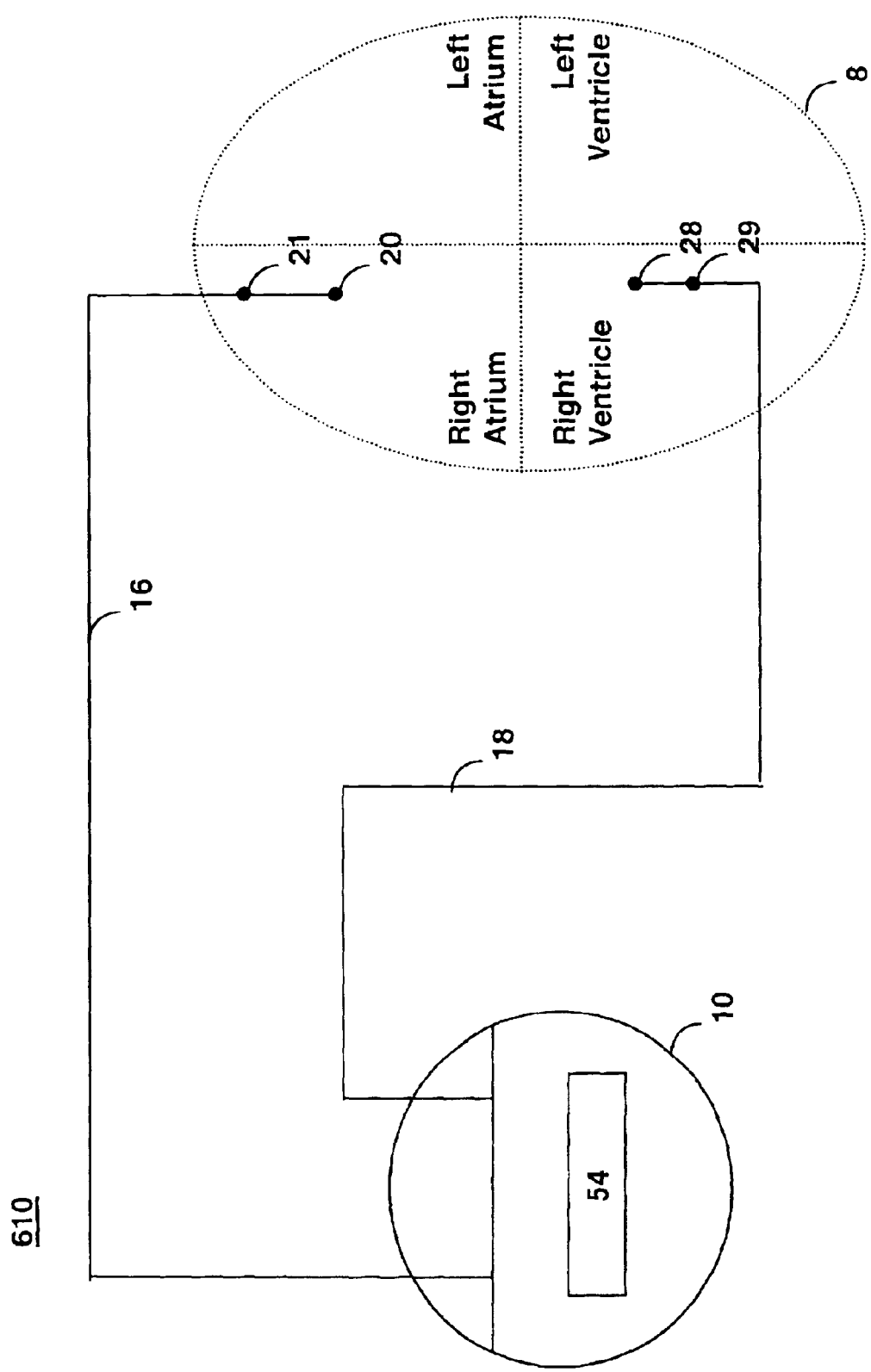
FIG. 6 is a schematic view of one embodiment of an implantable medical device for comparison with the present invention.

FIG. 6 is a simplified schematic view of one embodiment of an implantable medical device ("IMD") 10 for comparison with the embodiments of the present invention.

IMD 10 is connected to heart 8 through a series of leads 16 and 18. In the embodiment of FIG. 6, lead 18 couples a ventricular circuit to the right ventricle; however, lead 18 could also be coupled to the left ventricle. Ventricular circuit may provide for the sensing and stimulation of the ventricle in any suitable manner as is known in the art and described above. Lead 18 may be, for example a unipolar endocardial lead as described above or any suitable lead well known in the art. Lead 18 features two electrodes 28 and 29 at its distal end. Electrodes 28, 29 may be used for stimulation of one of the ventricles, in the case of FIG. 6, the right ventricle. In the embodiment of FIG. 6, lead 16 couples an atrial circuit to the right atrium; however, lead 16 could also be coupled to the left atrium. Atrial circuit may provide for the sensing and stimulation of the atria in any suitable manner as is known in the art and described above. Lead 16 may be, for example, a unipolar endocardial lead as described above or any suitable lead well known in the art. Lead 16 features two electrodes 20 and 621 at its distal end. Electrodes 20, 21 may be used for stimulation of one of the atria, in the case of FIG. 6, the right atria.

Input/output circuit 54 of IMD 10 may be configured to sense cardiac activity in each of the respective chambers and also to provide electrical stimulation in response thereto.

Figure 7:
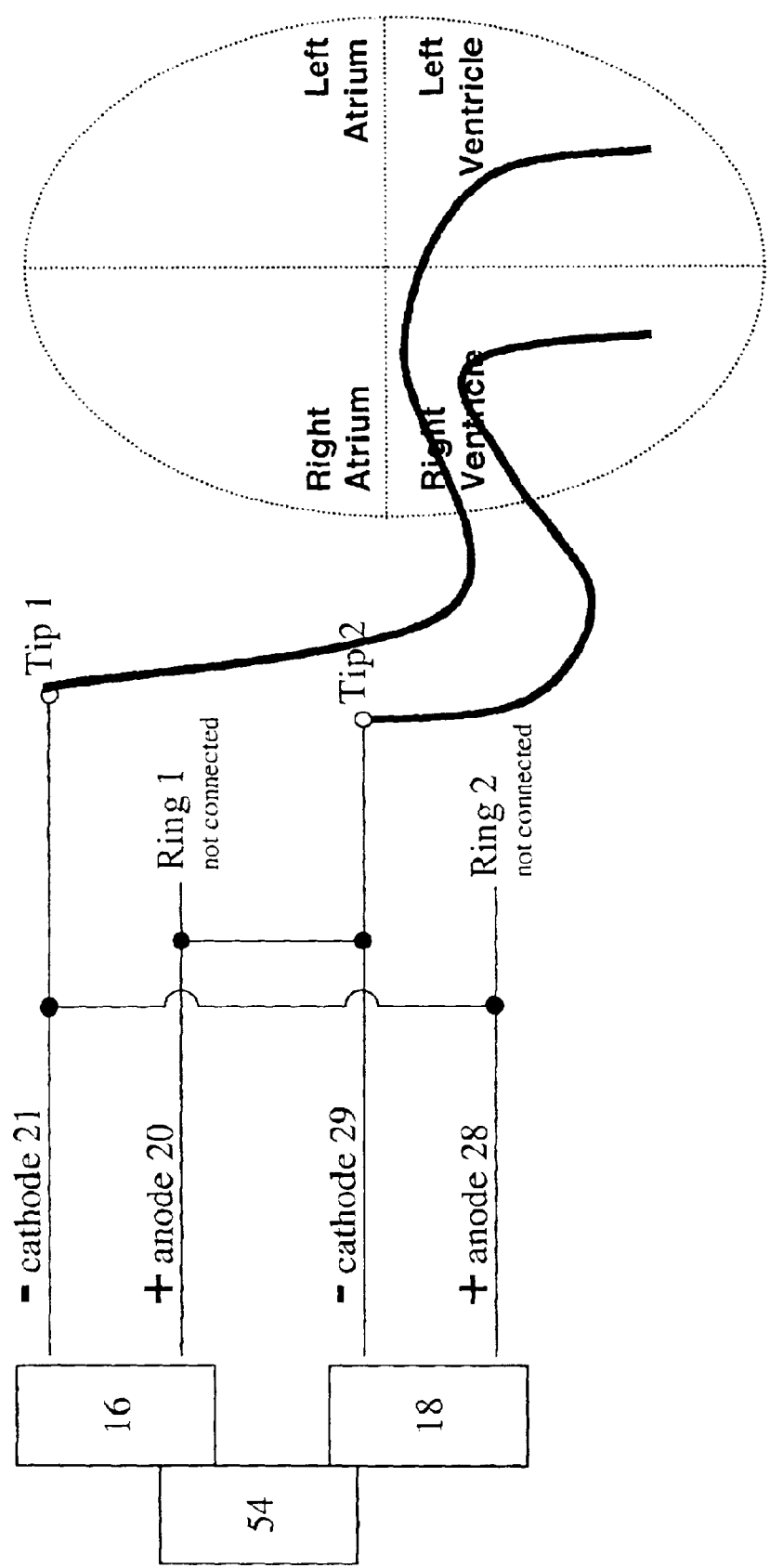
FIG. 7 is a schematic view illustrating components of one embodiment of an implantable medical device, made in accordance with the present invention.

FIG. 7 is a simplified schematic view of one embodiment of an implantable medical device ("IMD") 10 in accordance with the present invention.

Pacing leads 16 and 18 extend from connector header module 12 to the left and right ventricles, respectively, of heart 8. In one embodiment of the invention, leads 16, 18 are selectively insertable into connector header module 12 depending on the desired configuration (i.e., the leads are inserted in one configuration to provide the embodiment of FIG. 7 and in other configurations to provide other embodiments.) For example, the leads may be coupled prior to implantation. Lead 18 couples an input/output circuit 54 of IMD 10 to the right ventricle. Input/output circuit 54 may provide for the sensing and stimulation of the ventricles in any suitable manner as is known in the art and described above. Lead 18 may be, for example a unipolar endocardial lead as described above or any suitable lead well known in the art. Lead 18 may comprise two ventricular electrodes 28 and 29 at its distal end. In the embodiment of FIG. 7, electrode 29 serves as a cathode and is coupled to the right ventricle. Meanwhile, electrode 28 serves as an anode to electrode 29 and is not connected with the circuit or is not in use for this configuration.

Lead 16 couples input/output circuit 54 of IMD 10 to the left ventricle. Input/output circuit 54 may provide for the sensing and stimulation of the ventricles in any suitable manner as is known in the art and described above. Lead 16 may be, for example, a unipolar endocardial lead as described above or any suitable lead well known in the art. Lead 16 may comprise two atrial electrodes 20 and 21 at its distal end. In the embodiment of FIG. 7, electrode 21 serves as a cathode and is coupled to the left ventricle. Meanwhile, electrode 20 serves as an anode to electrode 21 and is not connected with the circuit or is not in use for this configuration.

Input/output circuit 54 of IMD 10 may be configured to sense cardiac activity in each of the respective chambers and also to provide electrical stimulation in response thereto. For example, input/output circuit 54 may be configured to disable connectivity of electrode 28 and/connectivity of electrode 20 to accomplish the configuration shown in FIG. 7 (i.e., where electrodes 28, 20 are "not connected"). In some embodiments of the invention, the switch matrix may accomplish a switch from a unipolar lead configuration to a bipolar lead configuration as described above. Such a switch may be accomplished using switching transistors and circuitry disposed within IMD 10.

Figure 8:
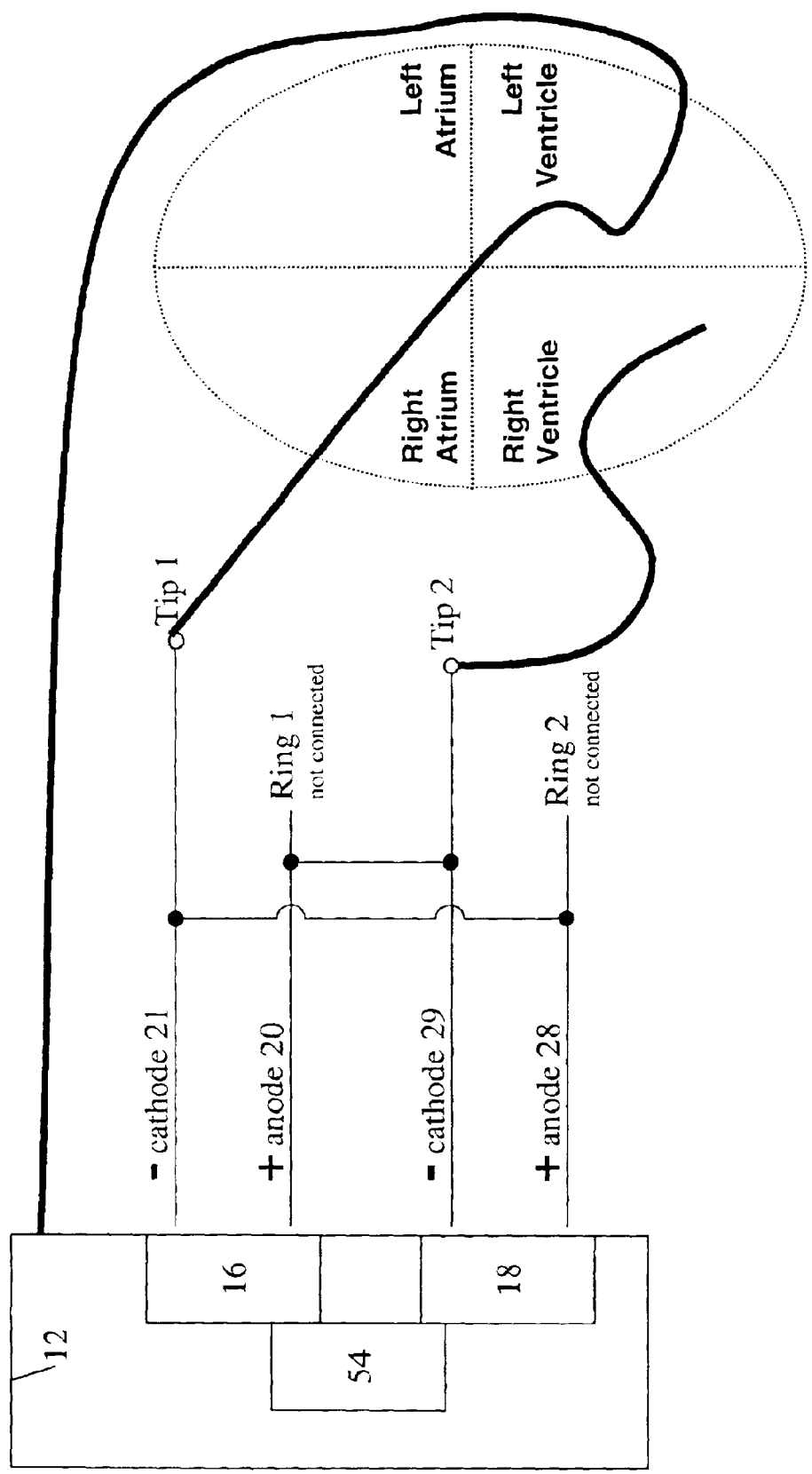
FIG. 8 is a schematic view illustrating one configuration of the components of the embodiment of the implantable medical device of FIG. 7.

FIG. 8 is a simplified schematic view of another configuration for the embodiment of IMD 10 shown in FIG. 7. With the configuration shown in FIG. 8, unipolar pacing stimulation may be delivered to the right ventricle. Additionally, sensing pulses may be delivered to either of the ventricles in a unipolar or bipolar fashion.

For example, in the embodiment shown in FIG. 8, the right ventricle will receive a unipolar pacing pulse from cathode 29 while the left ventricle into which cathode 21 has been placed will not receive a pacing pulse. That is, the pathway of current from cathode 21 may be, for example, through the heart muscle wall through the body to connector header module 12. In the embodiment of FIG. 8, electrode 28 is not connected with the circuit or is not in use for this configuration. Meanwhile, electrode 20 is also not connected with the circuit or is not in use for this configuration.

Input/output circuit 54 of IMD 10 may be configured to sense cardiac activity in each of the respective chambers and also to provide electrical stimulation in response thereto. For example, input/output circuit 54 may be configured to route connectivity of electrode 21 to connector header module 12 and to disable connectivity of electrode 28 and/connectivity of electrode 20 to accomplish the configuration shown in FIG. 8 (i.e., where electrodes 28, 20 are "not connected"). Such a switch may be accomplished using switching transistors and circuitry disposed within IMD 10.

Figure 9:
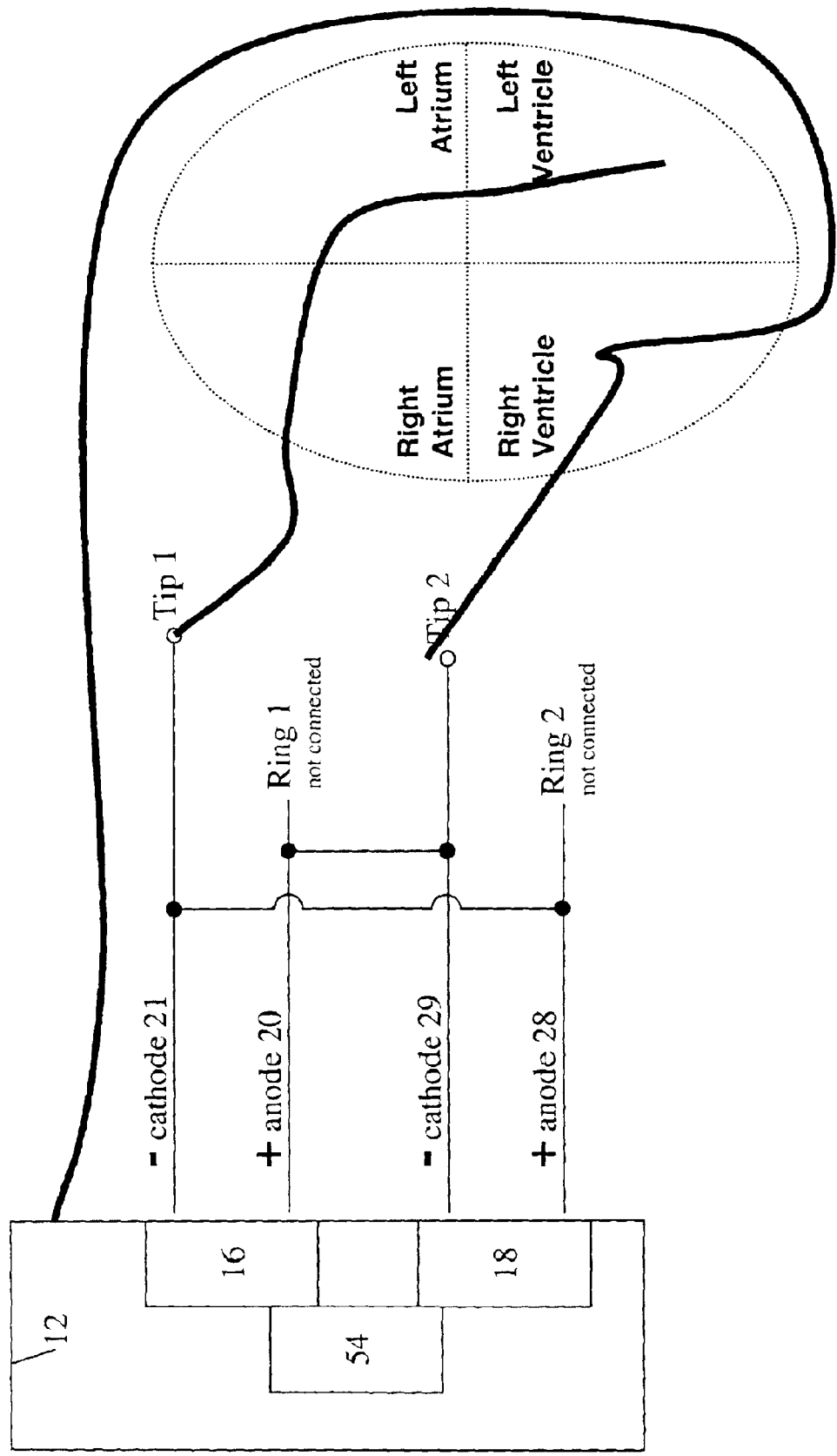
FIG. 9 is a schematic view illustrating one configuration of the components of the embodiment of the implantable medical device of FIG. 7.

FIG. 9 is a simplified schematic view of another configuration for the embodiment of IMD 10 shown in FIG. 7. With the configuration shown in FIG. 9, unipolar pacing stimulation may be delivered to the left ventricle. Additionally, sensing pulses may be delivered to either of the ventricles in a unipolar or bipolar fashion.

For example, in the embodiment shown in FIG. 9, the left ventricle will receive a unipolar pacing pulse from cathode 21 while the right ventricle into which cathode 29 has been placed will not receive a pacing pulse. That is, the pathway of current from cathode 29 may be, for example, through the heart muscle wall through the body to connector header module 12. In the embodiment of FIG. 9, electrode 28 is not connected with the circuit or is not in use for this configuration. Meanwhile, electrode 20 is also not connected with the circuit or is not in use for this configuration.

Input/output circuit 54 of IMD 10 may be configured to sense cardiac activity in each of the respective chambers and also to provide electrical stimulation in response thereto. For example, input/output circuit 54 may be configured to route connectivity of electrode 21 to connector header module 12 and to disable connectivity of electrode 28 and/connectivity of electrode 20 to accomplish the configuration shown in FIG. 9 (i.e., where electrodes 28, 20 are "not connected"). Such a switch may be accomplished using switching transistors and circuitry disposed within IMD 10.

Figure 10:
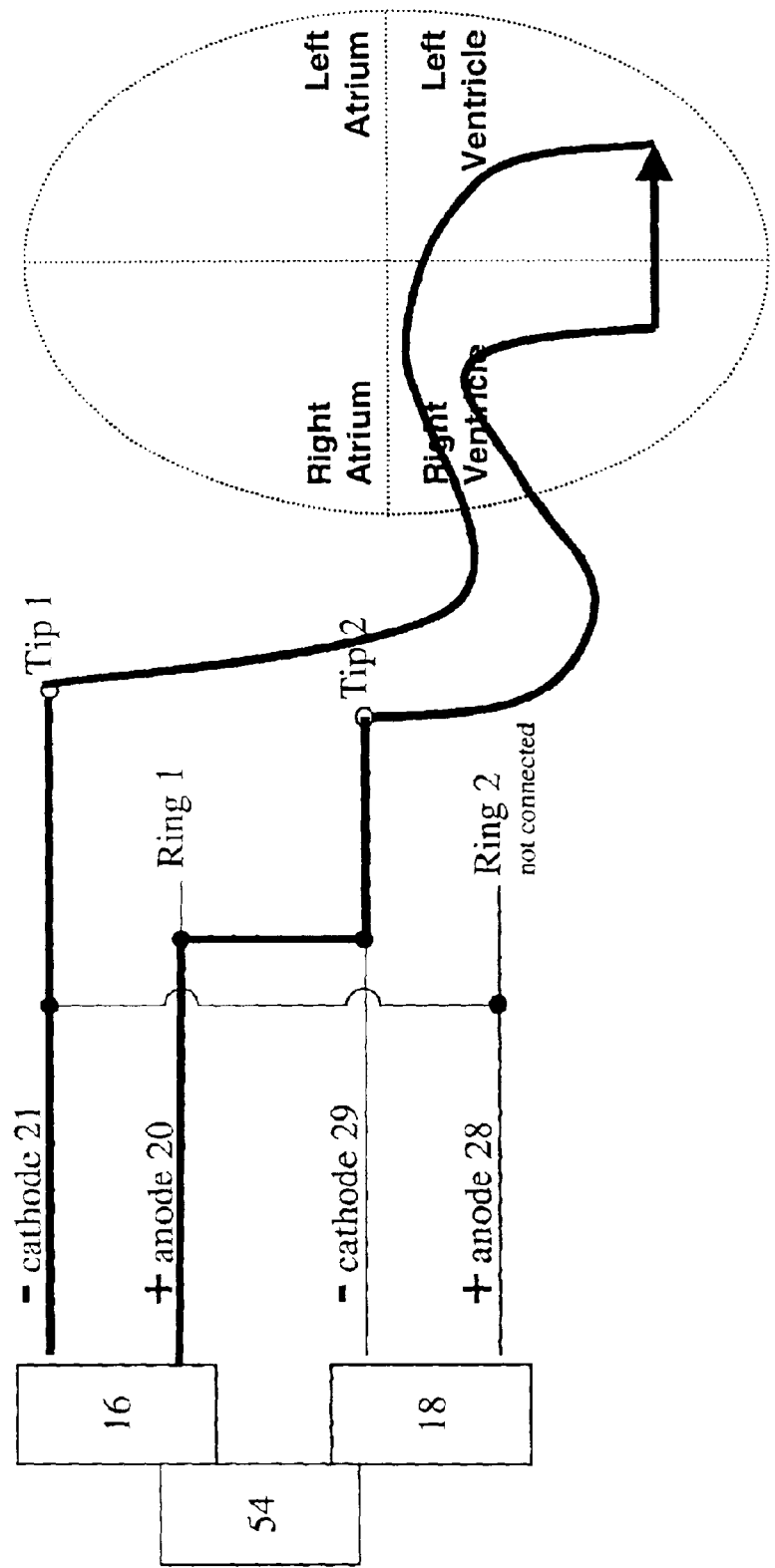
FIG. 10 is a schematic view illustrating one configuration of the components of the embodiment of the implantable medical device of FIG. 7.

FIG. 10 is a simplified schematic view of another configuration for the embodiment of IMD 10 shown in FIG. 7. With the configuration shown in FIG. 10, bipolar pacing stimulation may be achieved in both ventricular chambers, with delivery from the right to the left ventricle. Additionally, sensing pulses may be delivered to either of the ventricles in a unipolar or bipolar fashion.

Pacing leads 16 and 18 extend from connector header module 12 to the left and right ventricles, respectively, of heart 8. In one embodiment of the invention, leads 16, 18 are selectively insertable into connector header module 12 depending on the desired configuration (i.e., the leads are inserted in one configuration to provide the embodiment of FIG. 10 and in other configurations to provide other embodiments.) For example, the leads may be coupled prior to implantation. Lead 18 couples an input/output circuit 54 of IMD 10 to the right ventricle. Input/output circuit 54 may provide for the sensing and stimulation of the ventricles in any suitable manner as is known in the art and described above. Lead 18 may be, for example a unipolar endocardial lead as described above or any suitable lead well known in the art. Lead 18 may comprise two ventricular electrodes 28 and 29 at its distal end. In the embodiment of FIG. 10, electrode 21 serves as a cathode and is coupled to the left ventricle. Meanwhile, electrode 29 serves as an anode to electrode 21 and is coupled to the right ventricle while electrode 20 serves to complete the circuit to electrode 29. Finally, electrode 28 is not connected with the circuit or is not in use for this configuration.

Input/output circuit 54 of IMD 10 may be configured to sense cardiac activity in each of the respective chambers and also to provide electrical stimulation in response thereto. For example, input/output circuit 54 may be configured to route connectivity of electrode 20 to electrode 29 and to disable connectivity of electrode 28 to accomplish the configuration shown in FIG. 9 (i.e., where electrode 28 is "not connected").

Figure 11:
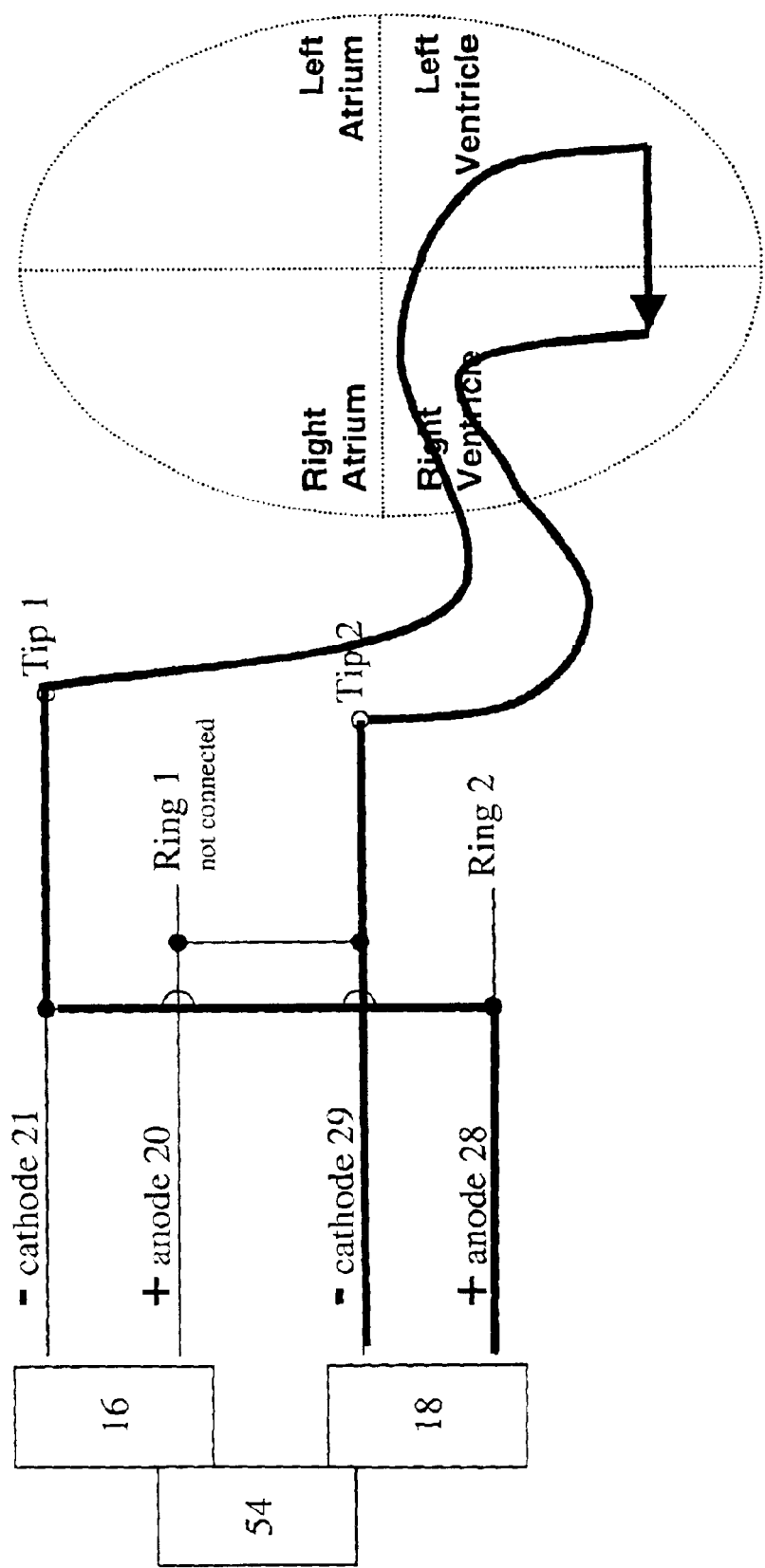
FIG. 11 is a schematic view illustrating one configuration of the components of the embodiment of the implantable medical device of FIG. 7.

FIG. 11 is a simplified schematic view of another configuration for the embodiment of IMD 10 shown in FIG. 7. With the configuration shown in FIG. 11, bipolar pacing stimulation may be achieved in both ventricular chambers, with delivery from the left to the right ventricle. Additionally, sensing pulses may be delivered to either of the ventricles in a unipolar or bipolar fashion.

In the embodiment of FIG. 11, electrode 29 serves as a cathode and is coupled to the right ventricle. Meanwhile, electrode 21 serves as an anode to electrode 29 and is coupled to the left ventricle while electrode 28 serves to complete the circuit to electrode 21. Finally, electrode 20 is not connected with the circuit or is not in use for this configuration.

Input/output circuit 54 of IMD 10 may be configured to sense cardiac activity in each of the respective chambers and also to provide electrical stimulation in response thereto. For example, input/output circuit 54 may be configured to route connectivity of electrode 28 to electrode 21 and to disable connectivity of electrode 20 to accomplish the configuration shown in FIG. 11 (i.e., where electrode 20 is "not connected").

As can be seen from the above, the configurations of the electrodes 20 and 28 which are not directly connected to the heart, and of electrodes 21 and 28 disposed in opposing ventricles of the heart, are switchable. Moreover, the polarity of various electrodes is selectable or switchable. In the embodiments described in FIGS. 6–10, the leads employed are unipolar. In alternate embodiments of the invention, bipolar leads may be employed as well. Additionally, electrodes 20, 21 and electrodes 28, 29 may be similarly disposed in opposing atria of the heart.

Figure 12:
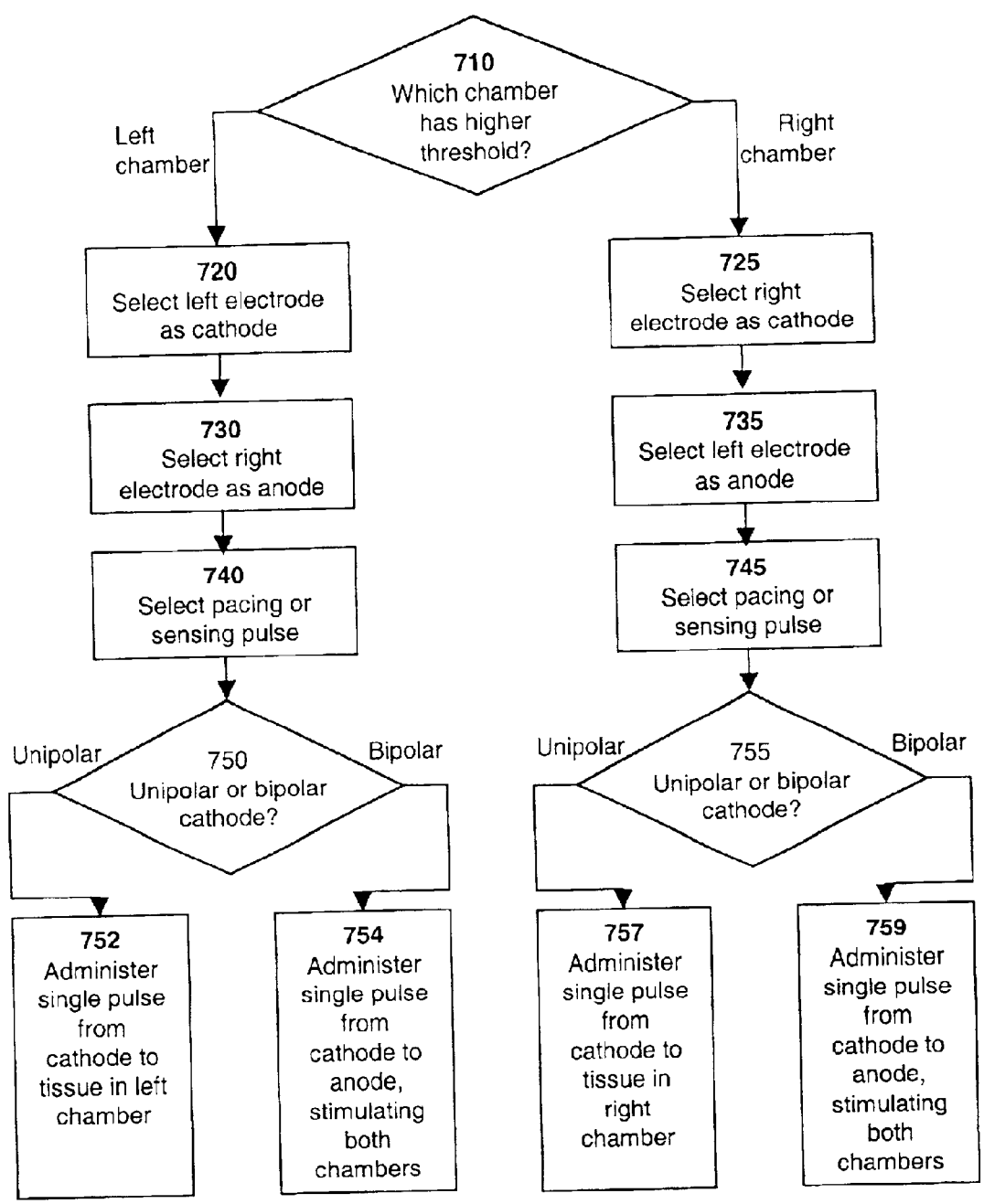
FIG. 12 is a flow diagram of one embodiment of a method for stimulating a heart in accordance with the present invention.

FIG. 12 shows one embodiment of a method for stimulating a heart in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

As shown at block 710, it may be determined which chamber of a left and a right chamber of heart 8 requires the higher threshold pacing pulse. This determination may be made, for example, by comparing the required threshold pacing pulse for the right atrium to the required threshold pacing pulse for the left atrium and vice versa. Alternatively, the required threshold pacing pulse for the right ventricle may be compared to the required threshold pacing pulse for the left ventricle and vice versa.

The cathode may be assigned to the chamber that requires the higher threshold. In some embodiments of the invention, threshold measurements are taken and the chamber requiring higher threshold pacing pulses is automatically assigned the cathode. This assignment may be made automatically, for example by a computer algorithm and/or program capable of being stored in an electronic medium such as, by way of example only, RAM 68 or ROM 70 of IMD 10, where the contents of RAM 68 and ROM 70 may be accessed and consequently executed by microprocessor 64/microcomputer 58. Alternatively, a physician may manually assign the cathode.

Once the cathode has been assigned, the method of the present invention may proceed according to two paths such as, for example, those shown in FIG. 12. In the first path, beginning at block 720, the electrode in the left chamber is assigned as the cathode. At block 730, the electrode in the right chamber is then assigned as the anode. At block 740, it is determined whether the stimulation pulse will be a pacing or a sensing pulse. At block 750, it is determined whether the cathode will act as a unipolar electrode or as a bipolar electrode. If, as seen at block 752, the cathode will act as a unipolar electrode, a single pulse will be administered from the cathode to tissue within the left chamber. If, as seen at block 754, the cathode will act as a bipolar electrode, a single pulse will be administered from the cathode to the anode, thus simultaneously administering stimulation to tissue in both the left and the right chambers.

In the second path, beginning at block 725, the electrode in the right chamber is assigned as the cathode. At block 735, the electrode in the left chamber is then assigned as the anode. At block 745, it is determined whether the stimulation pulse will be a pacing or a sensing pulse. At block 755, it is determined whether the cathode will act as a unipolar electrode or as a bipolar electrode. If, as seen at block 757, the cathode will act as a unipolar electrode, a single pulse will be administered from the cathode to tissue within the right chamber. If, as seen at block 759, the cathode will act as a bipolar electrode, a single pulse will be administered from the cathode to the anode, thus simultaneously administering stimulation to tissue in both the left and the right chambers.

In some embodiments of the invention, the pacing mode may determine in which direction the stimulus is administered, i.e., whether the stimulation is administered from the right atrium to the left atrium or from the left atrium to the right atrium, the right ventricle to the left ventricle or from the left ventricle to the right ventricle. The mode may further determine the type of sensing configuration of the electrodes. Table 2 lists some examples of modes, the resulting direction of the stimulation pulse, and the resulting sensing configuration of the electrodes.

TABLE 2

| MODE | SENSING | PACING | PULSE DELIVERED |
| --- | --- | --- | --- |
| $V_2 V_2 I$ (FIG. 7) | Bipolar | Unipolar | bipolar sensing stimulation delivered from left electrode to left ventricle AND right electrode to right ventricle unipolar pacing stimulation delivered from left electrode to left ventricle and right electrode to right ventricle |
| $V_1 V_1 I$ (FIG. 8) | Unipolar | Unipolar | unipolar sensing stimulation delivered from right electrode to right ventricle (unused electrode is routed to pacemaker can) unipolar pacing stimulation delivered from right electrode to right ventricle (unused electrode is routed to pacemaker can) |
| $V_1 V_1 I$ (FIG. 9) | Unipolar | Unipolar | unipolar sensing stimulation delivered from left electrode to left ventricle (unused electrode is routed to pacemaker can) unipolar pacing stimulation delivered from left electrode to left ventricle (unused electrode is routed to pacemaker can) |
| $V_{12} V_{12} I$ (FIG. 10) | bipolar | bipolar | bipolar sensing stimulation delivered from right electrode to left ventricle bipolar sensing stimulation delivered from right electrode to left ventricle |
| $V_{21} V_{21} I$ (FIG. 11) | bipolar | bipolar | bipolar sensing stimulation delivered from left electrode to right ventricle bipolar sensing stimulation delivered from left electrode to right ventricle |

In some embodiments of the invention, once the proper polarities and electrode assignments of the leads have been established, bipolar stimulation may proceed in a first direction, i.e., from a first opposing chamber to a second opposing chamber. For example, stimulation may proceed from the left ventricle to the right ventricle. In such cases, simultaneous pacing stimulation occurs.

Alternatively, some embodiments may provide unipolar stimulation. In some embodiments, a unipolar stimulation pulse may be delivered in each chamber and followed very quickly by one or more successive stimulation pulses. The successive stimulation pulse may be administered for example any suitable time after the first pulse, for example from 0 to 100 msecs, 10 to 90 msecs, 20 to 80 msecs or 30 to 70 msecs after the first stimulation pulse is administered. Such staggered stimulation permits the induced contractions of the opposing chamber to be optimized from a hemodynamic perspective. That is, pumping efficiency and output of the heart may be increased by use of slight inter-chamber timing delays between two opposing chambers of heart 8, such as between the two ventricles or between the two atria.

Figure 13:
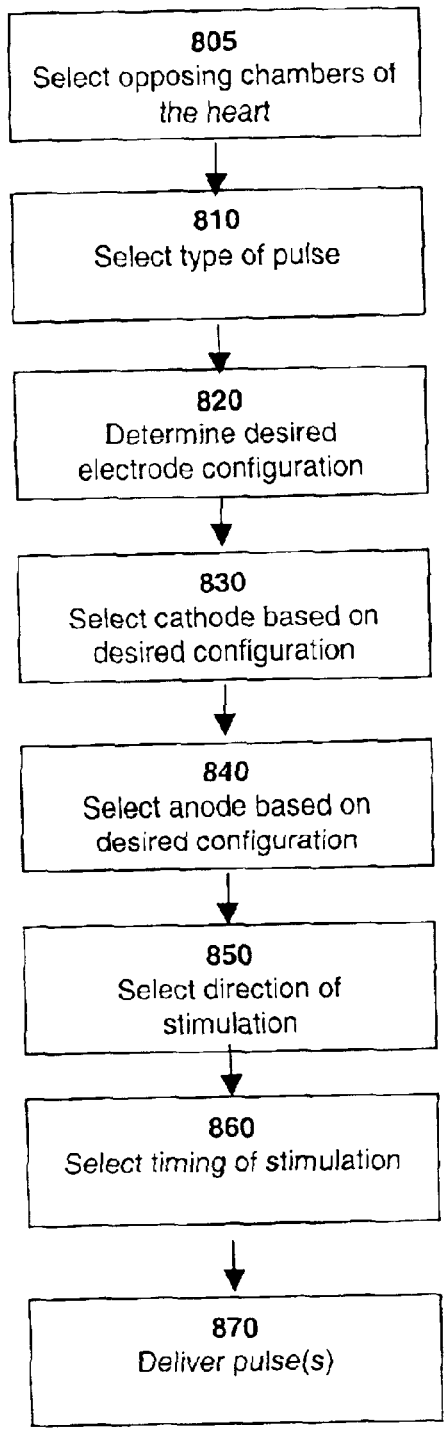
FIG. 13 is a flow diagram of another embodiment of a method for stimulating a heart in accordance with the present invention.

FIG. 13 shows another embodiment of a method for stimulating a heart in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

As seen at block 805 and described above, the opposing chambers of the heart in which the electrodes are to be disposed is selected. At least one first electrode and at least one second electrode may be disposed in the selected opposing chambers of the heart. For example, the right and left atria may be selected or the right and left ventricles.

As seen at block 810 and described above, a type of pulse may be selected. For example a pacing pulse or a sensing pulse may be selected.

At block 820, a desired electrode configuration is determined based on the type of stimulation desired. For example, the electrode configuration may result in unipolar pacing of the left or right ventricle, unipolar sensing of the left or right ventricle, bipolar pacing of the left or right ventricle, bipolar sensing of the left or right ventricle, unipolar pacing of the left or right atria, unipolar sensing of the left or right atria, bipolar pacing of the left or right atria, bipolar sensing of the left or right atria.

At block 830 an appropriate cathode is selected based on the desired electrode configuration and at block 840 an appropriate anode is selected based on the desired configuration. For example, in FIG. 8, electrode 29 is the cathode and electrode 28 is the anode resulting in an electrode configuration which delivers unipolar pacing of the right ventricle. In FIG. 9, electrode 21 is the cathode and electrode 20 is the anode resulting in an electrode configuration that delivers unipolar pacing of the left ventricle.

An additional parameter may be selected at block 850 to determine the direction of the stimulus being delivered. For example, In FIG. 10, electrode 21 is the cathode and electrode 29 is the anode resulting in an electrode configuration that delivers bipolar pacing from the right to the left ventricle. In FIG. 11, electrode 29 is the cathode and electrode 21 is the anode resulting in an electrode configuration that delivers bipolar pacing from the left to the right ventricle. Other electrode configurations are possible, including corresponding sensing unipolar and bipolar electrode configurations.

At block 860, the timing of the stimulation may be selected. For example, the electrodes may deliver simultaneous stimulation or staggered stimulation.

At block 870, the stimulation pulse is delivered. More than one pulse may be delivered based on selections made in the preceding steps.

In the embodiment of the invention seen in FIGS. 6 through 13, the parameters determined include: pacing of the right atrium, sensing of the right atrium, pacing of the left atrium, sensing of the left atrium, pacing of the right ventricle, sensing of the right ventricle, pacing of the left ventricle, sensing of the left ventricle, bipolar stimulation or unipolar stimulation, simultaneously delivered pulses or pulses delivered in a staggered fashion. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the increase of pacing parameters, per se, but may find further application as a measuring means. The present invention further includes within its scope methods of making and using the measurement means described hereinabove. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method of pacing opposing chambers of a heart with a pacing system, the pacing system comprising a first unipolar medical electrical lead having at least one first electrode configured for positioning in a first opposing chamber of the heart, a second unipolar medical electrical lead having at least one second electrode configured for positioning in a second opposing chamber of the heart, an implantable pulse generator operably connected to the first and second unipolar medical electrical leads, the implantable pulse generator further comprising an hermetically sealed housing capable at serving as a can electrode, and means for switching electrode configurations between the first electrode and the can electrode, between the second electrode and the can electrode, between the first electrode and the second electrode and between the second electrode and the first electrode, the method comprising:

determining a primary electrode configuration;

selecting a cathode from the first electrode, the second electrode and the can electrode based on the primary electrode configuration;

selecting an anode from the first electrode, the second electrode and the can electrode based on the primary electrode configuration;

delivering a first pulse between the cathode and the anode;

determining a first threshold of the first opposing chamber;

determining a second threshold of the second opposing chamber; and selecting the first electrode as the cathode if the first threshold is higher than the second threshold.

2. The method of claim 1, further comprising:
determining an alternate electrode configuration;
selecting an alternate cathode from the first electrode, the second electrode and the can electrode based on the alternate electrode configuration;
selecting an alternate anode from the first electrode, the second electrode and the can electrode based on the alternate electrode configuration; and
delivering a second pulse between the alternate cathode and the alternate anode.

3. The method of claim 2, further comprising:
re-selecting the cathode and the anode;
delivering a third pulse between the cathode and the anode;
re-selecting the alternate cathode and the alternate anode; and
delivering a fourth pulse between the alternate cathode and the alternate anode.

4. The method of claim 1, further comprising:
delivering the first pulse between the cathode and the anode so that the direction of the pulse occurs from the first opposing chamber to the second opposing chamber.

5. The method of claim 1, further comprising:
delivering the first pulse between the cathode and the anode so that the direction of the pulse occurs from the second opposing chamber to the first opposing chamber.

6. The method of claim 1, further comprising:
delivering the first pulse between the cathode and the anode in a first direction; and
delivering at least one subsequent pulse between the cathode and the anode in the first direction.

7. The method of claim 1, further comprising:
delivering the first pulse from the cathode; and
simultaneously delivering a second pulse from the anode.

8. A method of pacing opposing chambers of a heart with a pacing system, the pacing system comprising a first unipolar medical electrical load having at least one first electrode configured for positioning in a first opposing chamber of the heart, a second unipolar medical electrical lead having at least one second electrode configured for positioning in a second opposing chamber of the heart, an implantable pulse generator operably connected to the first and second unipolar medical electrical leads, the implantable pulse generator further comprising an hermetically sealed housing capable of serving as a can electrode, the method comprising:
determining a primary electrode configuration;
selecting a cathode from the first electrode, the second electrode and the can electrode based on the primary electrode configuration;
selecting an anode from the first electrode, the second electrode and the can electrode based on the primary electrode configuration;
delivering a first pulse between the cathode and the anode;
determining a first threshold of the first opposing chamber;
determining a second threshold of the second opposing chamber; and
selecting the first electrode as the cathode if the first threshold is higher than the second threshold.

9. The method of claim 8, further comprising:
determining an alternate electrode configuration;
selecting an alternate cathode from the first electrode, the second electrode and the can electrode based on the alternate electrode configuration;
selecting an alternate anode from the first electrode, the second electrode and the can electrode based on the alternate electrode configuration; and
delivering a second pulse between the alternate cathode and the alternate anode.

10. The method of claim 9, further comprising:
re-selecting the cathode and the anode;
delivering a third pulse between the cathode and the anode;
re-selecting the alternate cathode and the alternate anode; and
delivering a fourth pulse between the alternate cathode and the alternate anode.

11. The method of claim 8, further comprising:
delivering the first pulse between the cathode and the anode so that the direction of the pulse occurs from the first opposing chamber to the second opposing chamber.

12. The method of claim 8, further comprising:
delivering the first pulse between the cathode and the anode so that the direction of the pulse occurs from the second opposing chamber to the first opposing chamber.

13. The method of claim 8, further comprising:
delivering the first pulse between the cathode and the anode in a first direction; and
delivering at least one subsequent pulse between the cathode and the anode in the first direction.

14. An implantable medical system, comprising:
a pulse generator;
a first unipolar medical electrical lead operably connected to the pulse generator, the first unipolar medical electrical lead having at least one first electrode configured for positioning in a first opposing chamber of the heart;
a second unipolar medical electrical lead operably connected to the pulse generator, the second unipolar medical electrical lead having at least one second electrode configured for positioning in a second opposing chamber of the heart;
selecting means for selecting at least one of the first electrode, the second electrode and the can electrode, wherein a primary electrode configuration is determined and a cathode is selected with the selecting means, an anode is selected with the selecting means and a pulse is delivered by the pulse generator between the cathode and the anode;
means for determining a first threshold of the first opposing chamber;
means for determining a second threshold of the second opposing chamber; and
means for selecting the first electrode as the cathode if the first threshold is higher than the second threshold.

15. The system of claim 14, further comprising:
means for determining an alternate electrode configuration;
means for selecting an alternate cathode from the first electrode, the second electrode and the can electrode based on the alternate electrode configuration;
means for selecting an alternate anode from the first electrode, the second electrode and the can electrode based on the alternate electrode configuration; and means for delivering a second pulse between the alternate cathode and the alternate anode.

16. The system of claim 15, further comprising:
means for re-selecting the cathode and the anode;
means for delivering a third pulse between the cathode and the anode;
means for re-selecting the alternate cathode and the alternate anode; and
delivering a fourth pulse between the alternate cathode and the alternate anode.

17. The system of claim 14, further comprising:
means for delivering the first pulse between the cathode and the anode so that the direction of the pulse occurs from the first opposing chamber to the second opposing chamber.

18. The system of claim 14, further comprising:
means for delivering the first pulse between the cathode and the anode so that the direction of the pulse occurs from tie second opposing chamber to the first opposing chamber.

19. The system of claim 14, further comprising:
means for delivering the first pulse between the cathode and the anode in a first direction; and
means for delivering at least one subsequent pulse between the cathode and the anode in the first direction.

* * * * *

UNITED STATES PATENT AND TRADEMARK OFFICE
CERTIFICATE OF CORRECTION

PATENT NO. : 6,950,701 B2 Page 1 of 1
APPLICATION NO. : 10/024226
DATED : September 27, 2005
INVENTOR(S) : Malcolm J. Begemann et al.

It is certified that error appears in the above-identified patent and that said Letters Patent is hereby corrected as shown below:

Col. 19, line 42, delete "electrical load having" and insert --electrical lead having--.

Col. 22, line 4, delete "from tie second" and insert --from the second--.

Signed and Sealed this

Twenty-sixth Day of December, 2006

JON W. DUDAS
*Director of the United States Patent and Trademark Office*